(12) United States Patent
Putz

(10) Patent No.: US 8,594,793 B2
(45) Date of Patent: Nov. 26, 2013

(54) ELECTRICAL CONNECTOR WITH CANOPY FOR AN IN-BODY MULTI-CONTACT MEDICAL ELECTRODE DEVICE

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 1419 days.

(21) Appl. No.: 11/943,013

(22) Filed: Nov. 20, 2007

(65) Prior Publication Data

US 2009/0132016 A1   May 21, 2009

(51) Int. Cl.
*A61N 1/00*   (2006.01)
(52) U.S. Cl.
USPC .......................................................... 607/37
(58) Field of Classification Search
USPC ................ 607/37, 38; 439/668, 669, 909
See application file for complete search history.

(56) References Cited

U.S. PATENT DOCUMENTS

| | | | |
|---|---|---|---|
| 4,379,462 A | 4/1983 | Borkan et al. | |
| 4,461,304 A | 7/1984 | Kuperstein | |
| 4,516,820 A | 5/1985 | Kuzma | |
| 4,633,889 A | 1/1987 | Talalla et al. | |
| 4,676,258 A | 6/1987 | Inokuchi et al. | |
| 4,712,557 A | 12/1987 | Harris | |
| 4,735,208 A | 4/1988 | Wyler et al. | |
| 4,744,371 A * | 5/1988 | Harris | 607/117 |
| 4,850,359 A | 7/1989 | Putz | |
| 4,869,255 A | 9/1989 | Putz | |
| 5,097,835 A | 3/1992 | Putz | |
| 5,560,358 A | 10/1996 | Arnold et al. | |
| 5,902,236 A | 5/1999 | Iversen | |
| 6,415,168 B1 | 7/2002 | Putz | |
| 6,671,534 B2 | 12/2003 | Putz | |
| 7,134,919 B2 | 11/2006 | Putz | |
| 2002/0177363 A1 * | 11/2002 | Wu et al. | 439/668 |

* cited by examiner

*Primary Examiner* — Scott Getzow
(74) *Attorney, Agent, or Firm* — Jansson Munger McKinley & Shape Ltd.

(57) ABSTRACT

An electrical connector for connecting a multi-contact medical electrode device with a plural-contact tail. Having a tail-receiving first elongate member with a tail-receiving void and a second elongate member. The second elongate member has a nesting surface and an array of electrical conductors which are spring-loaded pin plunger devices. The spring-loaded pin plunger devices having movable pins that project into the tail-receiving void. The second elongate member also having at least one canopy extending from the nesting surface and over a respective electrical conductor, the canopy being configured for snap-engagement with the notch whereby the canopy holds in place the respective linear-array plural-contact tail through locking frictional engagement.

8 Claims, 6 Drawing Sheets

ELECTRICAL CONNECTOR WITH CANOPY FOR AN IN-BODY MULTI-CONTACT MEDICAL ELECTRODE DEVICE

FIELD OF THE INVENTION

This invention is related generally to electrical connectors for use in the medical field and, more particularly, to medical connectors for implantable multi-contact medical electrode devices.

BACKGROUND OF THE INVENTION

Multi-contact medical electrode devices are placed in the human body for various purposes, such as brain-mapping in epilepsy treatment. In such treatments wires generally extend from the multi-contact medical electrode to a plural-contact tail. The plural-contact tail is linear in shape and contains an array of sleeve-like contacts spaced therealong. The plural contacts of the plural-contact tail are to facilitate quick electrical connection of the contacts of the multi-contact medical electrode device such as for monitoring, recording and analysis purposes. Connectors have been configured to simultaneously engage the contacts of the plural-contact tail for their individual electrical connection to separate wire strands which emerge from the connector.

Various connectors have been developed to facilitate plural-contact connection. Examples of such prior art plural-contact medical connectors are those disclosed in the following U.S. Pat. No. 4,850,359 (Putz), U.S. Pat. No. 4,869,255 (Putz), U.S. Pat. No. 6,415,168 (Putz), U.S. Pat. No. 4,744,371 (Harris), U.S. Pat. No. 5,560,358 (Arnold et al.), U.S. Pat. No. 5,902,236 (Iversen), U.S. Pat. No. 4,516,820 (Kuzma), U.S. Pat. No. 4,712,557 (Harris), U.S. Pat. No. 4,461,304 (Kuperstein), U.S. Pat. No. 4,379,462(Borkan et al.), U.S. Pat. No. 4,633,889 (Talalla et al.) and U.S. Pat. No. 4,676,258 (Inokuchi et al.).

Some medical connectors of the prior art have a number of shortcomings. Medical connectors for use in patients who have a seizure tendency must be secure. If a patient has a seizure there is the chance that the electrical connections could be destroyed or disrupted. Specifically, the plural-contact tails of multi-contact electrodes can become dislodged or broken by the involuntary movements that occur during a seizure. Therefore, it is important that the connector be secure so that it can withstand the jerking motions that are characteristic of seizures.

In certain prior art devices the electrical connector is a connector of the type that does not provide a secure connection and, therefore, the connector can become dislodged or broken. If a connector does become dislodged or broken it can result in a significant loss of information and time.

In summary, there are problems and shortcomings in prior connectors for use with multi-contact medical electrode devices.

OBJECTS OF THE INVENTION

It is an object of this invention to provide a connector for multi-contact medical, electrode devices overcoming some of the problems and shortcomings associated with the prior art.

Another object of the invention is to provide a multi-contact medical connector which is secure given the involuntary jerking motions which are customary with a seizure condition.

These and other objects of the invention will be apparent from the following descriptions and from the drawings.

SUMMARY OF THE INVENTION

This invention is an electrical connector for an in-body multi-contact medical electrode device with at least one canopy which is used in combination with a linear-array plural-contact tail.

The multi-contact medical connector of this invention is a connector of the type that includes a tail-receiving first elongate member having proximal and distal ends and a second elongate member with corresponding proximal and distal ends. The first elongate member has a presentation face which extends along the second elongate member and the first elongate member also includes a tail-receiving void. The presentation face is parallel to the void and has notches therealong intersecting with the void to expose the plural tail contacts in the void. The second elongate member has a nesting surface and an array of electrical conductors therealong. At least one canopy extends from the nesting surface of the second elongate member and over a respective electrical conductor, the canopy being configured for snap-engagement with the notch whereby the canopy holds in place the linear-array plural-contact tail through locking frictional engagement.

Preferably, the nesting surface includes two faces set at right angles to one another; a pivot-axis-adjacent face and a pivot-axis-opposite face. It is also preferred that the presentation face is substantially parallel to the pivot-axis-opposite face when the first elongate member is in the closed position.

It is highly preferred that each canopy is fixed to the pivot-axis-opposite face. Also highly preferred is that each canopy is integrally formed with the pivot-axis-opposite face. In preferred embodiments, each canopy partially encircles a respective one of the electrical conductors.

Most preferred is where the electrical conductors are pin plunger devices which protrude beyond the nesting surface toward the first elongate member. Preferably, the presentation face and the nesting surface abut one another to define the closed position. In highly preferred embodiments, the presentation face has a lead edge which is adjacent to the nesting surface when the first elongate member is in the closed position. In certain embodiments, the notches on the presentation face extend to the lead edge such that the notches receive the pin plunger devices and engage the at least one canopy as the first elongate member is pivoted to the closed position.

The medical connector of this invention has significant advantages over connectors of the prior art. The connector has at least one canopy which provides locking frictional engagement so that the linear-array plural-contact tail is held in place when the connector is in the closed position. This allows the connector to provide excellent security.

The invention includes the medical connector as described above, and also includes the combination of the connector with the linear-array plural-contact tail of a multi-contact medical electrode device.

BRIEF DESCRIPTION OF THE DRAWINGS

The drawings illustrate a preferred embodiment including the above-noted characteristics and features of the invention. The invention will be readily understood from the descriptions and drawings. In the drawings.

DETAILED DESCRIPTION OF PREFERRED EMBODIMENTS

Figure 1:
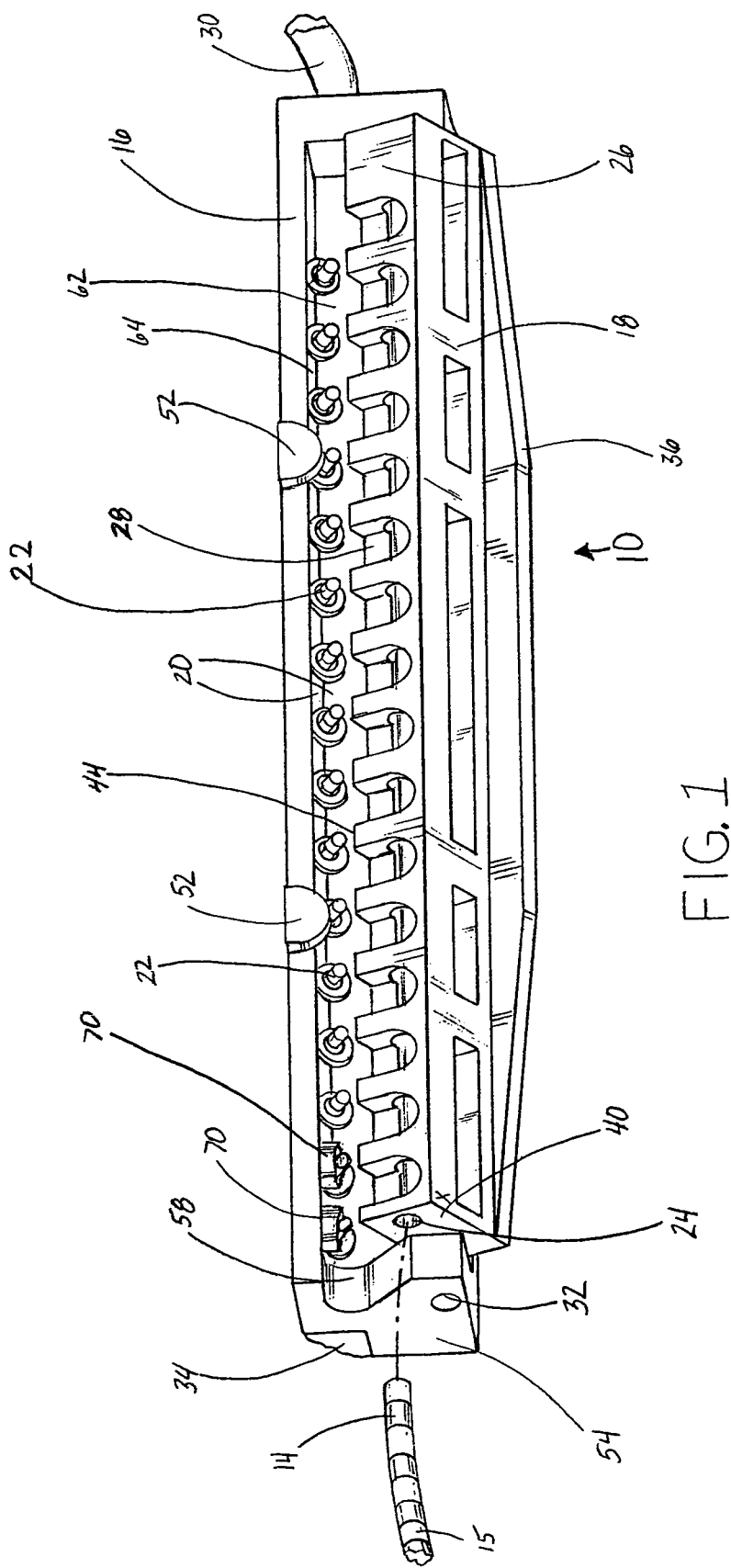
FIG. 1 is a perspective view of the connector with two canopies in an open position, with the plural-contact tail of an in-body medical electrode in position for insertion into the connector.

FIGS. 1-6 illustrate an electrical connector 10 for connecting the linear-array plural-contact tail 12 of an in-body multi-contact medical electrode (the in-body portion of which is not shown), having a linear array of electrical contacts 14 spaced therealong, each electrically linked by a small electrical wire running up and beyond tail 12 to a particular in-body contact on the in-body portion of the electrode. Connector 10 includes first and second elongate members 18 and 16 which are pivotable with respect to one another about a pivot axis A which extends along their lengths.

FIGS. 1-6 illustrate that first elongate member 18 extends along the length of second elongate member 16 and includes a linear tail-receiving void 24, a presentation face 26 which is parallel with and closely adjacent to void 24, and notches 28 along presentation face 26. The notches 28 intersect with void 24 to expose contacts 14 of tail 12 at presentation face 26 in alignment with and intersecting, the pin 23 of spring-loaded pin plunger devices 22 as seen in FIGS. 1-3 and 7.

Figure 3:
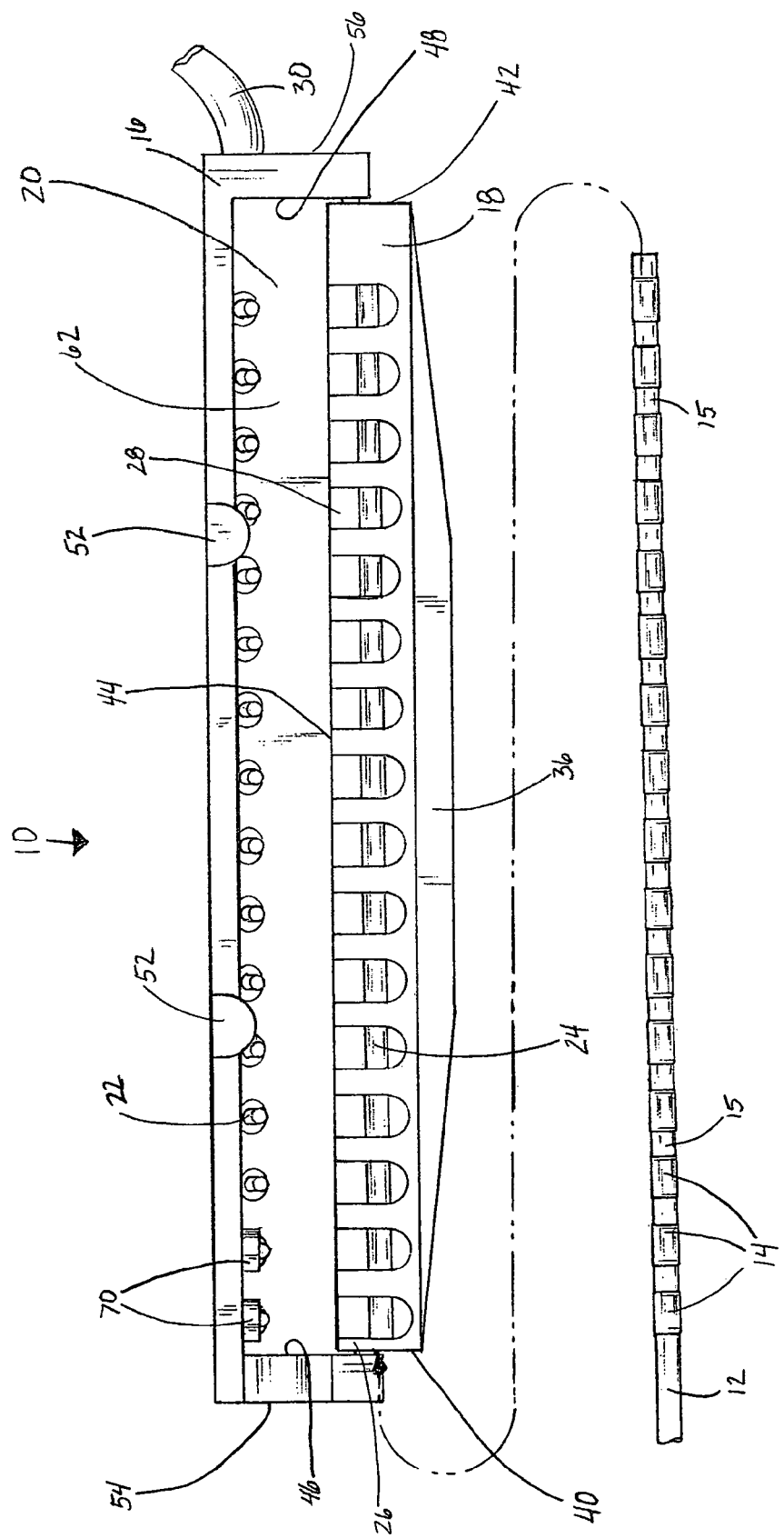
FIG. 3 is a front elevation of the connector of FIG. 1.

FIGS. 1 and 3 illustrate that second elongate member 16 has a nesting surface 20 which includes two faces set at right angles to one another, a pivot-axis-adjacent face 62 and a pivot-axis-opposite face 64. As seen in FIGS. 1 and 3, a linear array of spring-loaded pin plunger devices 22 are situated along the nesting surface 20 at the intersection of the pivot-axis-adjacent face 62 and pivot-axis-opposite face 64 and extend at an angle substantially parallel to the movement of the tail-receiving void 24 corresponding with the linear array of electrical contacts 14 of plural-contact tail 12.

FIGS. 1 and 3 illustrate that second elongate member 16 has nesting surface 20 and an array of electrical conductors therealong, preferably spring loaded pin plunger devices 22. As shown in FIGS. 1, 3 and 5-6, at least one canopy 70 extends from nesting surface 20 of second elongate member 16 and over a respective spring-loaded pin plunger device 22. Second elongate member 16 will have at least one canopy 70 but can also have many canopies 70 as illustrated in FIGS. 1 and 3. In some embodiments second elongate member 16 can have a canopy 70 corresponding to each spring-loaded pin plunger device 22.

Figure 6:
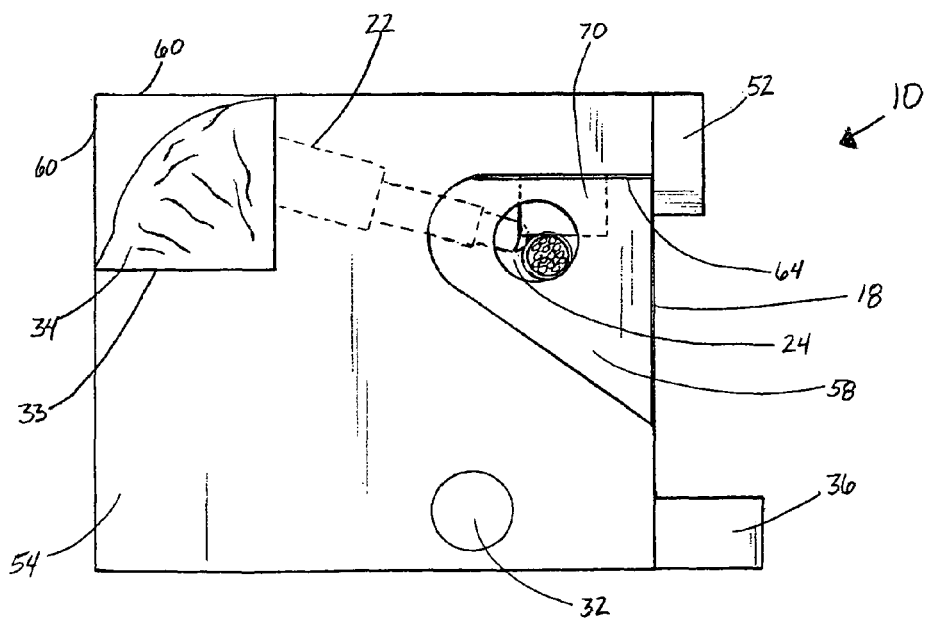
FIG. 6 is a left side elevation of the connector of FIG. 5, but with the connector fully closed.

Canopy 70 is configured for snap-engagement with the respective notch 28 whereby canopy 70 holds in place the linear-array plural-contact tail 12 through locking frictional engagement as seen in FIG. 6. Locking frictional engagement occurs between each canopy 70 and the linear-array plural-contact tail 12. Locking frictional contact also occurs between each canopy 70 and the presentation face 26 on the first elongate member 18.

As shown in FIGS. 1, 3 and 5-6, canopy 70 is fixed to the pivot-axis-opposite face 64. Canopy 70 is integrally formed with the pivot-axis-opposite face 64 as illustrated in FIGS. 1 and 3. The orientation of canopy 70 is such that canopy 70 partially encircles a respective one of the spring-loaded pin plunger devices 22 as illustrated in FIG. 1.

Figure 2:
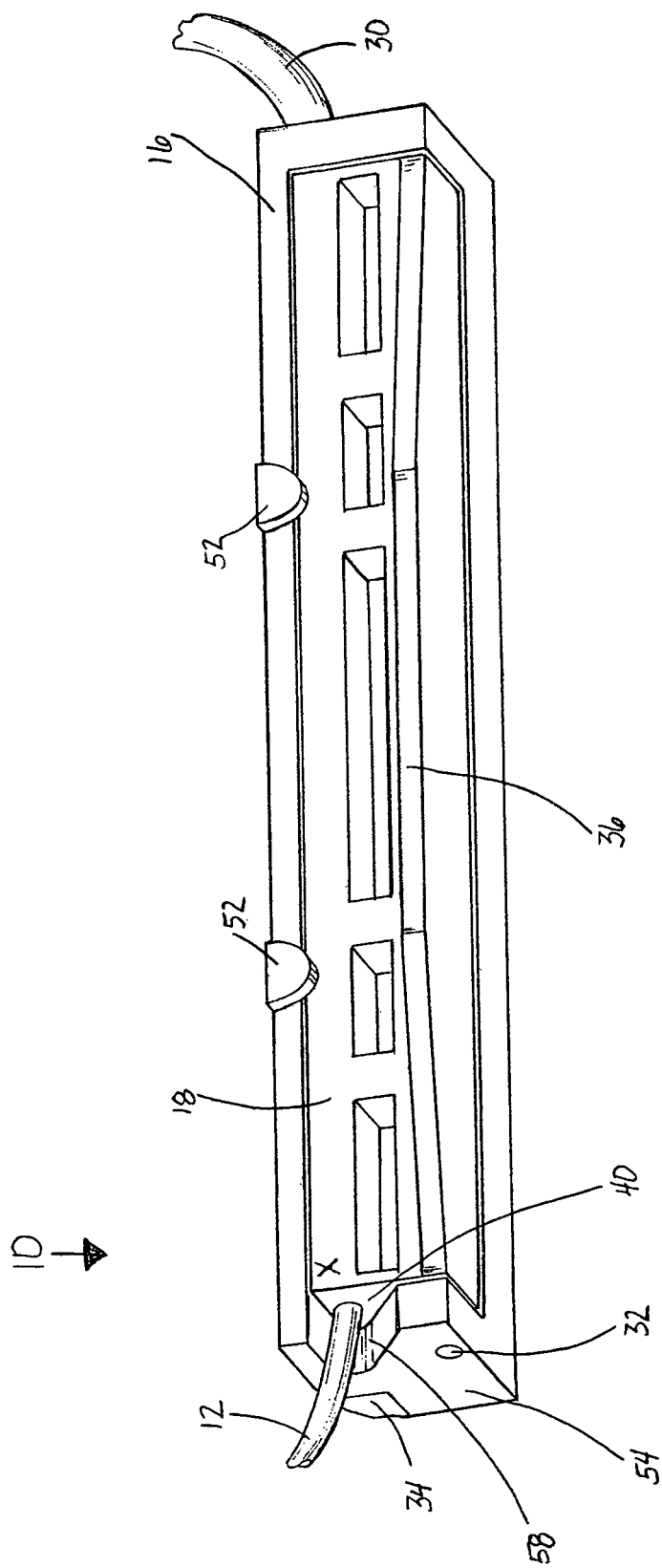
FIG. 2 is a perspective view of the connector of FIG. 1, but with the connector in the closed position.
Figure 4:
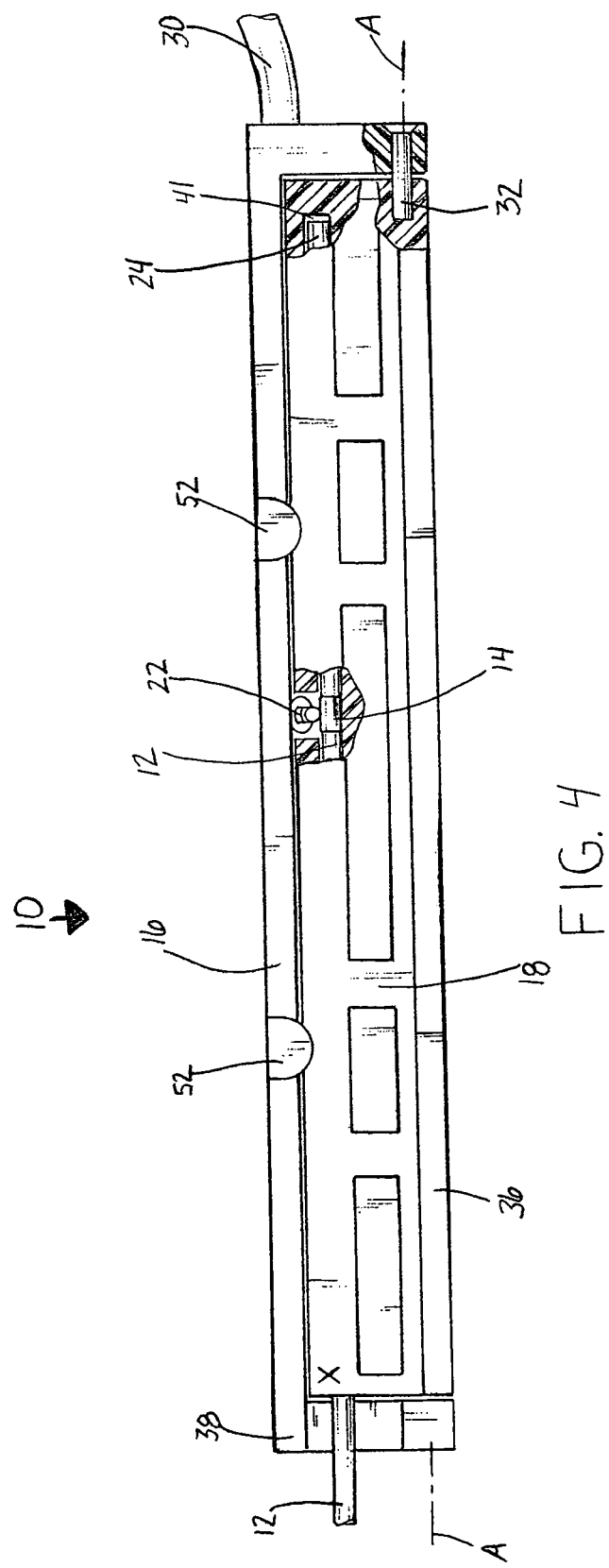
FIG. 4 is a front elevation of the connector of FIG. 2, but with cutaway portions to illustrate certain internal details.
Figure 5:
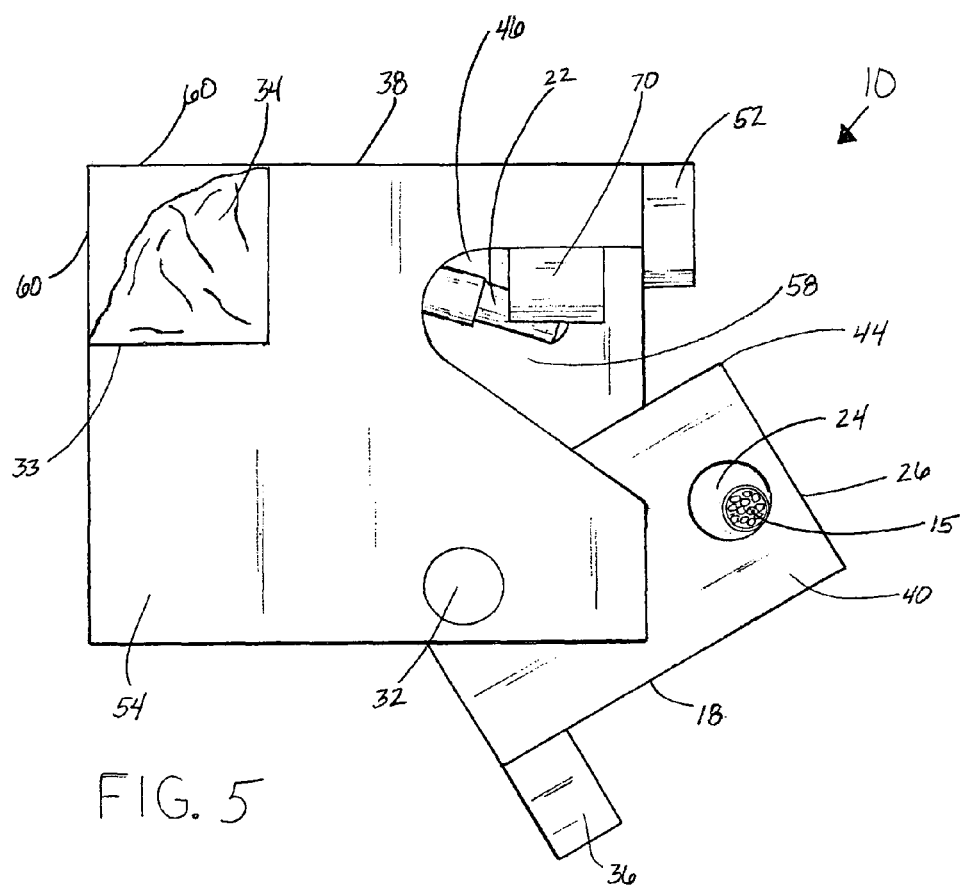
FIG. 5 is a left side elevation of the connector with a canopy, with the tail inserted, showing the connector just before it is closed.

First elongate member 18 pivots with respect to second elongate member 16 between an open position illustrated by FIGS. 1, 3 and 5 and a closed position illustrated by FIGS. 2, 4 and 6. Pivot pins 32 (see cutaway portion of FIG. 4) extend along axis A and pivotably connect first elongate member 18 with second elongate member 16. In the closed position, presentation face 26 is juxtaposed to nesting surface 20, such that contacts 14 are placed into engagement with spring-loaded pin plunger devices 22, each plunger device 22 is electrically connected to one of the wires which make-up the multi-wire electrical cable 30 which extends from the distal end 56 of the second elongate member 16 and which allows easy connection by means not shown with other equipment. Second elongate member 16 has distal end 56 and proximal end 54. Second elongate member 16 also has outer surface 38 as illustrated in FIG. 4.

Figure 8:
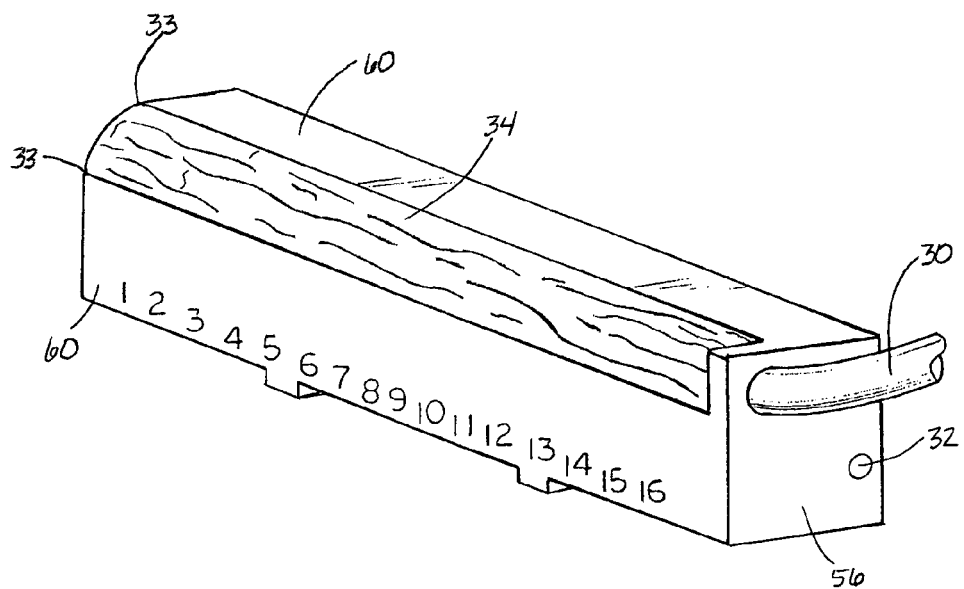
FIG. 8 is a back perspective view of the connector, with the channel and the body of epoxy-like substance.

Second elongate member 16 has an array of spring-loaded pin plunger devices 22 along its nesting surface 20 as illustrated in FIGS. 1 and 3. As shown in FIG. 1, the spring-loaded pin plunger devices 22 are situated therealong nesting surface 20 and extend at an angle substantially parallel to the movement of the tail-receiving void 24 at the point the pin 23 on the spring-loaded pin plunger device 22 enters therein to facilitate electrical engagement with plural contacts 14 on tail 12. The spring-loaded pin plunger devices 22 extend through second elongate member 16 to allow electrical connection with wires 30. Spring-loaded pin plunger devices 22 are potted in their positions and protrude beyond nesting surface 20 (see cutaway portion of FIG. 4). The wires which make-up the multi-wire electrical cable 30 extend into channel 33 filled with an epoxy-like substance 34 as seen in FIGS. 5-6 and 8.

First elongate member 18 has proximal and distal ends 40 and 42, and linear void 24 extends from an opening at proximal end 40 to a stop 41 near distal end 42 as illustrated in FIGS. 1-3. The position of stop 41 is fixed such that full insertion of tail 12 into void 24 causes contacts 14 to be in alignment with notches 28 along presentation face 26 of first elongate member 18 as illustrated in FIGS. 1-4. FIGS. 1-4 show that second elongate member 16 includes a pair of opposed inwardly-facing endwalls 46 and 48 between which first elongate member 18 extends in nested fashion, with ends 40 and 42 adjacent to endwalls 46 and 48, respectively. As shown in FIGS. 5 and 6, endwall 46, which is adjacent to proximal end 40 of first elongate member 18, is formed with an electrode tail access area 58 to accommodate the presence of electrode tail 12 during pivoting movement of first elongate member 18.

First elongate member 18 includes an integrally-formed grip flange 36 (see FIGS. 5 and 6), which extends away from pivot axis A (pivot axis A is shown in FIG. 4). To open connector 10, downward thumb pressure is applied on grip flange 36 to pivot first elongate member 18 away from the closed position shown in FIG. 6. Second elongate member 16 has at least one lock tab 52 which is positioned so that it overlaps first elongate member 16, thereby securing connector 10 in the closed position as illustrated in FIG. 2.

As shown best in FIG. 3, presentation face 26 has a lead edge 44. Notches 28 are located on lead edge 44 of presentation face 26. This provides a lateral opening to each notch 28 to receive spring-loaded pin plunger devices 22 as first elongate member 18 is pivoted to the closed position.

Figure 7:
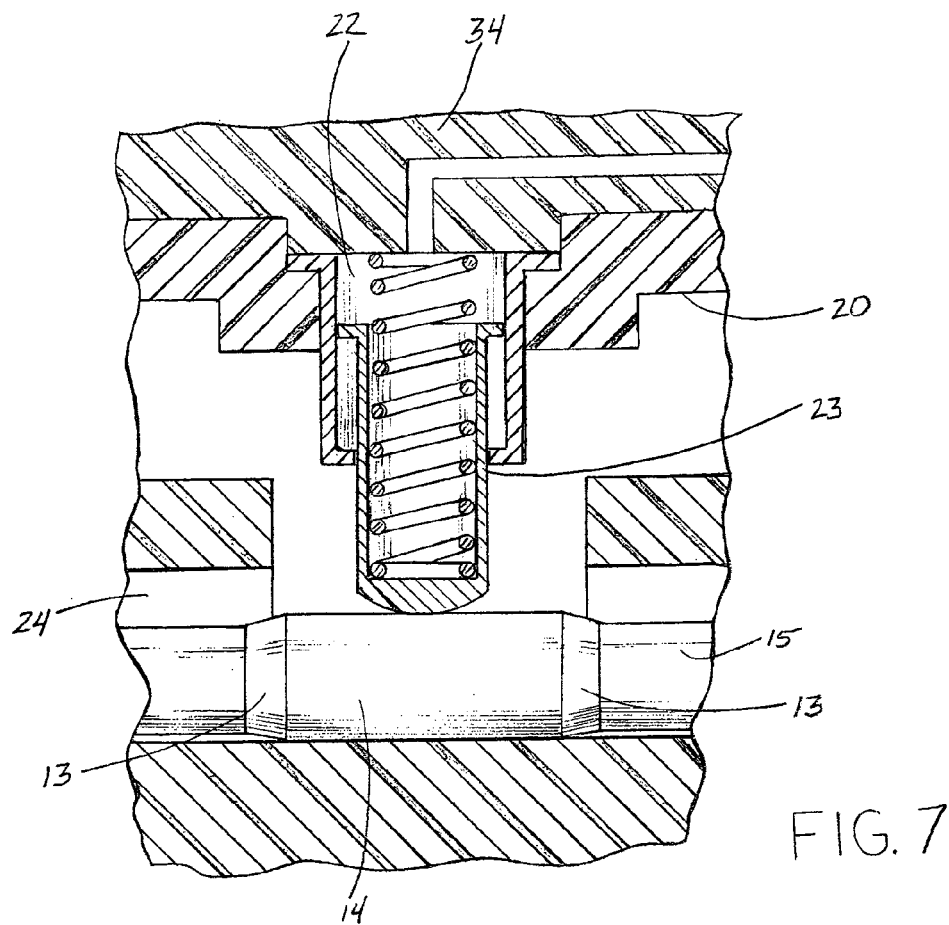
FIG. 7 is an enlarged fragmentary cutaway view of a portion of the connector of FIG. 4, as indicated in FIG. 4.

FIG. 7 illustrates details of contacts 12 and their relationship to pin 23 portion of spring-loaded pin plunger devices 22.

Each contact 14 of plural-contact tail 12 is an annular sleeve which includes necked-in ends 13, formed by crimping. As can be seen, the outer diameter of contact sleeves 14 are slightly greater than the outer diameter of the adjacent support tube 15 along which contacts 14 are mounted.

FIG. 8 illustrates channel 33, where the wires from the multi-wire electrical cable 30 are embedded, is filled with an epoxy-like substance 34 which is contained entirely between the second elongate member 16 and the intersecting planes 60.

First and second elongate members 18 and 16 of medical connector 10 may be made of hard plastic materials, a wide choice of which is available and will be apparent to those receiving this disclosure. First elongate member 18 is preferably made of translucent or transparent material so that the positions of contacts 14 can be seen even without looking at the notches 28. A wide variety of materials is available for the various parts discussed and illustrated herein.

While the principles of this invention have been described in connection with specific embodiments, it should be understood clearly that these descriptions are made only by way of example and are not intended to limit the scope of the invention.

The invention claimed is:

1. In an electrical connector for connecting a linear-array plural-contact tail of an in-body multi-contact medical electrode device, including (a) a tail-receiving first elongate member having proximal and distal ends, the first elongate member forming a tail-receiving void and having a presentation face which is parallel to the void and has notches therealong intersecting with the void to expose the plural tail contacts in the void and (b) a second elongate member with corresponding proximal and distal ends and having a nesting surface and an array of electrical conductors therealong, the nesting surface including a pivot-axis-adjacent face and a pivot-axis-opposite face substantially perpendicular thereto, the improvement comprising at least one canopy extending from and being fixed to the pivot-axis-opposite face of the nesting surface and over a respective electrical conductor and partially encircling the respective electrical conductor, the canopy being configured for snap-engagement with the notch whereby the canopy holds in place the linear-array plural-contact tail and the presentation face on the first elongate member in a closed position through locking frictional engagement.

2. The multi-contact medical connector of claim 1 wherein, the presentation face is substantially parallel to the pivot-axis-opposite face when the first elongate member is in the closed position.

3. The multi-contact medical connector of claim 1 wherein each canopy is/are integrally formed with the pivot-axis-opposite face.

4. The multi-contact medical connector of claim 1 wherein:
the electrical conductors are pin plunger devices which protrude beyond the nesting surface toward the first elongate member;
the presentation face and the nesting surface abut one another to define the closed position;
the presentation face has a lead edge which is adjacent to the nesting surface when the first elongate member is in the closed position; and
the notches on the presentation face extend to the lead edge such that the notches receive the pin plunger devices and engage the at least one canopy as the first elongate member is pivoted to the closed position.

5. In combination, (a) an electrical connector comprising a tail-receiving first elongate member with an presentation face and an elongate void with the plural-contact tail received therein, the first elongate member also having a lead edge with notches therealong intersecting with the void to expose the plural tail contacts, and a second elongate member having a nesting surface and an array of spring-loaded pin plunger devices therealong, the nesting surface including a pivot-axis-adjacent face and a pivot-axis-opposite face substantially perpendicular thereto, and (b) a linear-array plural-contact tail inserted within the void, the improvement comprising at least one canopy extending from and being fixed to the pivot-axis-opposite face of the nesting surface and over a respective pin plunger device and partially encircling the respective pin plunger device, the canopy being configured for snap-engagement with the notch whereby the canopy holds in place the respective linear-array plural-contact tail and the presentation face on the first elongate member in a closed position through locking frictional engagement.

6. The multi-contact medical connector of claim 5 wherein, the presentation face is substantially parallel to the pivot-axis-opposite face when the first elongate member is in the closed position.

7. The multi-contact medical connector of claim 5 wherein each canopy is/are integrally formed with the pivot-axis-opposite face.

8. The multi-contact medical connector of claim 5 wherein:
the pin plunger devices protrude beyond the nesting surface toward the first elongate member;
the presentation face and the nesting surface abut one another to define the closed position;
the presentation lace has a lead edge which is adjacent to the nesting surface when the first elongate member is in the closed position; and
the notches on the presentation face extend to the lead edge such that the notches receive the pin plunger devices and engage the at least one canopy as the first elongate member is pivoted to the closed position.

* * * * *